United States Patent [19]

Fujii et al.

[11] Patent Number: 4,886,877
[45] Date of Patent: Dec. 12, 1989

[54] NOVEL 2'-DEOXY-5-SUBSTITUTED URIDINE DERIVATIVES, PROCESSES FOR PREPARING THE SAME AND ANTITUMOR AGENT CONTAINING THE SAME

[75] Inventors: Setsuro Fujii, Toyonaka; Jun-ichi Yamashita, Tokushima; Hiroshi Matsumoto, Tokushima; Setsuo Takeda, Tokushima; Tadafumi Terada, Tokushima; Mitsugi Yasumoto, Tokushima; Norio Unemi, Tokushima, all of Japan

[73] Assignee: Taiho Pharmaceutical Company Limited, Tokyo, Japan

[21] Appl. No.: 163,237

[22] Filed: Feb. 26, 1988

Related U.S. Application Data

[63] Continuation of Ser. No. 611,678, May 18, 1984, abandoned.

[30] Foreign Application Priority Data

May 23, 1983 [JP] Japan ................................. 58-91190
Sep. 14, 1983 [JP] Japan ................................ 58-170149
Sep. 14, 1983 [JP] Japan ................................ 58-170147

[51] Int. Cl.$^4$ ............................................. C07H 19/06
[52] U.S. Cl. ...................................................... 536/23
[58] Field of Search ........................................... 536/23

[56] References Cited

U.S. PATENT DOCUMENTS

4,472,386  9/1984  Kodama et al. ..................... 424/180

FOREIGN PATENT DOCUMENTS

2658672  6/1978  Fed. Rep. of Germany ........ 536/23
0113795  9/1981  Japan .................................... 536/23

OTHER PUBLICATIONS

DeClercq, Antiviral and Antitumor Activities of 5-Substituted 2'-Deoxyuridines, Meth and Find Exptl Clin Pharmacol 2(5), 253–57 (1980).

Primary Examiner—Johnnie R. Brown
Assistant Examiner—James Oliver Wilson
Attorney, Agent, or Firm—Armstrong, Nikaido, Marmelstein, Kubovcik & Murray

[57] ABSTRACT

Novel 2'-deoxy-5-substituted uridine derivative represented by the general formula,

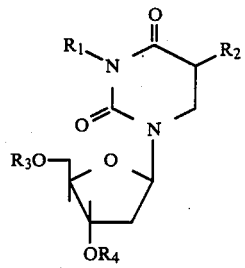

wherein $R_1$ is a hydrogen atom, a benzoyl group or a tetrahydrofuranyl group; $R_2$ is a fluorine atom or a trifluoromethyl group; and any one of $R_3$ and $R_4$ is a hydrogen atom and the other one is an alkyl group having 1 to 10 carbon atoms, an alkenyl group having 2 to 6 carbon atoms, a benzyl group having as the substituents selected from the group consisting of a halogen atom, an alkyl group having 1 to 4 carbon atoms, an alkoxy group having 1 to 4 carbon atoms and a nitro group, or an alkyl group having 1 to 3 carbon atoms having one or two phenyl groups as the substituents.

The novel 2'-deoxy-5-substituteduridine derivative possesses excellent antitumor activity with less toxicity, thus it is useful as antitumor agent.

18 Claims, No Drawings

NOVEL 2'-DEOXY-5-SUBSTITUTED URIDINE DERIVATIVES, PROCESSES FOR PREPARING THE SAME AND ANTITUMOR AGENT CONTAINING THE SAME

This application is a continuation of Ser. No. 611,678, filed May 18, 1984, now abandoned.

FIELD OF THE INVENTION

The present invention relates to a novel 2'-deoxy-5substituted uridine derivatives, processes for preparing the derivatives and antitumor agents containing the same as the active ingredient.

The novel 2'-deoxy-5-substituted uridine derivatives according to the present invention are represented by the general formula (I),

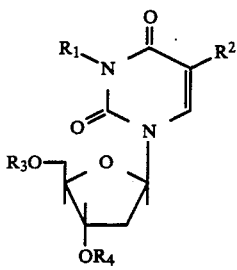

wherein $R_1$ is a hydrogen atom, a benzoyl group or a tetrahydrofuranyl group; $R_2$ is a fluorine atom or a trifluoromethyl group; and any one of $R_3$ and $R_4$ is a hydrogen atom and the other one is an alkyl group having 1 to 10 carbon atoms, an alkenyl group having 2 to 6 carbon atoms, a benzyl group having as the substituents selected from the group consisting of a halogen atom, an alkyl group having 1 to 4 carbon atoms, an alkoxy group having 1 to 4 carbon atoms and a nitro group, or an alkyl group having 1 to 3 carbon atoms having one or two phenyl group as the substituents.

CONSTITUTION OF PRIOR ART EXAMPLES AND PROBLEMS INVOLVED

2'-Deoxy-5-trifluoromethyl uridine (hereinafter referred to as $F_3TdR$) is reported as a compound first synthesized by Heiderberger et al. [Journal of American Chemical Society, Vol. 84, pp. 3597, (1962)].

It is reported that, $F_3TdR$ has an antitumor activity and that its therapeutic index for Adenocarcinoma 755 is superior than that of 2'-deoxy-5-fluorouridine (hereinafter referred to as FudR) [Cancer Research, Vol. 24, pp. 1979 (1964)]. Also it is known that $F_3TdR$ has a high antiviral activity [Cancer Research, Vol. 30, pp. 1549 (1970)].

For these reasons, various investigations have been made on the usefulness of $F_3TdR$ as a medicine. However, $F_3TdR$ has not yet shown any clinical effects, accordingly is not utilized as an antitumor agent.

On the other hand, it is reported that FudR has a very high carcinostatic activity in vitro, namely, a carcinostatic activity is as high as about 100 times that of 5-fluorouracil (hereinafter referred to as 5-FU) [C. Heiderberger: Proceedings of the Society for Experimental Biology & Medicine, Vol. 97, pp. 470 (1958)]. Further, FudR has been expected as a carcinostatic agent having higher effect, because FudR is converted, in vivo, into active-form of 5-fluoro-2'-deoxy-β-uridine-5'-monophosphate more easily than 5-FU. However, it is reported that, when FudR is administered in vivo, it is easily decomposed into 5-FU by nucleosidephosphorylase [G. D. Birnie, et al.: Biochimica et Biophysica Acta, Vol. 76, pp. 315 (1963)] and that FudR has a poor prolonged action in blood and is excreted very quickly and hence is inferior to 5-FU in carcinostatic effect [F. Kanzawa, et al., European Journal of Cancer, Vol. 16, pp. 1087 (1980)].

In addition, it is proved that FudR as a medicine is very toxic and has a small safety margin and that its administration is limited only to intra-arterial injection and no oral administration is possible which is a big handicap in actual cure [PHYSICIAN'S DESK REFERENCE, 32 edition, p. 1387, (1978)].

Under the above circumstances, on the basis of full understanding of the mechanisms and pharmacodynamics of expression of carcinostatic effects of FudR and $F_3TdR$, the present inventors made extensive studies in order to provide a compound of excellent properties which has a high carcinostatic activity in vivo and a large safety margin and can be orally administered.

As a result, it was found that novel compounds obtained by replacing the hydroxyl groups of the saccharide moiety of FudR or $F_3TdR$ with alkoxy groups meet the above object, have excellent carcinostatic activities and are useful as antitumor agents. Based on the findings, the present invention has been completed.

OBJECT OF THE PRESENT INVENTION

An object of the present invention is to provide a novel 2'-deoxy-5-substituted uridine derivative represented by the general formula (I), having antitumor activity.

Another object of the present invention is to provide processes for preparing said 2'-deoxy-5-substituted uridine derivative represented by the general formula (I).

Further object of the present invention is to provide antitumor agents containing said 2'-deoxy-5-substituted uridine derivative represented by the general formula (I) as the active ingredient.

CONSTITUTION OF THE PRESENT INVENTION (1) A novel 2'-deoxy-5-substituted uridine derivative represented by the general formula (I)

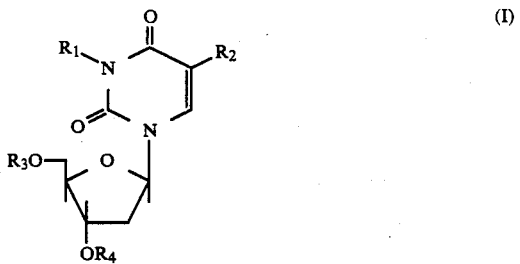

wherein $R_1$ is a hydrogen atom, a benzoyl group or a tetrahydrofuranyl group; $R_2$ is a fluorine atom or a trifluoromethyl group; and any one of $R_3$ and $R_4$ is a hydrogen atom and the other one is an alkyl group having 1 to 10 carbon atoms, an alkenyl group having 2 to 6 carbon atoms, a benzyl group having as the substituents selected from the group consisting of a halogen atom, an alkyl group having 1 to 4 carbon atoms, an alkoxy group having 1 to 4 carbon atoms and a nitro group, or an alkyl group having 1 to 3 carbon atoms having one or two phenyl groups as the substituents; (2) a process for producing said derivatives; and (3) antitumor agents containing said derivatives as the active ingredient.

In the above general formula (I), the alkyl group having 1 to 10 carbon atoms as defined in $R_3$ or $R_4$ is a straight-chain or a branched-chain alkyl group and specifically methyl, ethyl, propyl, isopropyl, butyl, sec-butyl, tert-butyl, pentyl, hexyl, heptyl, octyl, decyl group or the like, preferably an alkyl group having 1 to 6 carbon atoms; the alkenyl group having 2 to 6 carbon atoms is a straight-chain or a branched-chain alkenyl group and specifically is vinyl, allyl, 2-butenyl, 3-butenyl, 2-methyl-2-propenyl, 2-pentenyl, 5-hexenyl group or the like; the alkyl group having 1 to 4 carbon atoms as the substituent of the benzyl group is a straight-chain or a branched-chain alkyl group and specifically is methyl, ethyl, isopropyl, butyl, isobutyl, tert-butyl group or the like; the alkoxy group having 1 to 4 carbon atoms is a straight-chain or a branched-chain alkoxy group and specifically is methoxy, ethoxy, isopropoxy, butoxy, isobutoxy, tert-butoxy group or the like; the halogen atom is fluorine, chlorine, iodine or the like; and the alkyl group having 1 to 3 carbon atoms having one or two phenyl groups the substituents is benzyl, diphenylmethyl, α,α-dimethylbenzyl, 2-phenylethyl, 3-phenylpropyl, 2,2-diphenylethyl or α-methylbenzyl group or the like.

Among the compounds represented by the general formula (I), preferable compounds are:

(1) Compounds of the general formula (I) wherein $R_1$ is a hydrogen atom or a benzoyl group; $R_2$ is a fluorine atom or a trifluoromethyl group; and one of $R_3$ and $R_4$ is a hydrogen atom and the other one is an alkyl group having 1 to 6 carbon atoms or a benzyl group, and (2) Compounds of the general formula (I) wherein $R_1$ is a hydrogen atom, a benzoyl group or a tetrahydrofuranyl group; $R_2$ is a trifluoromethyl group; one of $R_3$ and $R_4$ is a hydrogen atom and the other one is a benzyl group having as the substituents selected from the group consisting of a halogen atom, an alkyl group having 1 to 4 carbon atoms, an alkoxy group having 1 to 4 carbon atoms and a nitro group, or an alkyl group having 1 to 3 carbon atoms having one or two phenyl groups as the substituents.

Next, processes for preparing derivatives of the present invention will be explained in detail.

Derivatives of the present invention represented by the general formula (I) can be prepared in various processes which differ dependent upon the kind of $R_1$ group of the general formula (I). That is, those derivatives of the present invention wherein $R_1$ of the general formula (I) is a benzoyl group or a tetrahydrofuranyl group can be obtained by reacting, for example, $F_3TdR$ or FudR as a starting material with benzoic acid halide or 2-chlorotetrahydrofuran, respectively, to form a 3-substituted-2'-deoxy-5-substituted uridine derivative represented by the general formula (II),

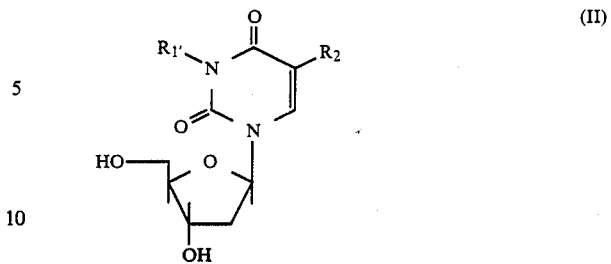

wherein $R_2$ is the same as defined above; and $R_1'$ is same as defined in $R_1$, provided that a hydrogen atom is excluded, and reacting the resulting uridine derivative of the general formula (II) with a halogen compound represented by the general formula (III),

RX (III)

wherein R is an alkyl group having 1 to 10 carbon atoms, an alkenyl group having 2 to 6 carbon atoms, a benzyl group having as substituents selected from the group consisting of a halogen atom, an alkyl group having 1 to 4 carbon atoms, an alkoxy group having 1 to 4 carbon atoms and a nitro group, or an alkyl group having 1 to 3 carbon atoms having one to two phenyl group as the substituents; and X is a chlorine atom, a bromine atom, an iodine atom or the like.

In the above process, preparation of a compound of the general formula (II), namely, the reaction of $F_3TdR$ or FudR with a benzoic acid halide or 2-chlorotetrahydrofuran can be conducted in accordance with usual methods which will be described in Reference Examples as mentioned below.

The reaction of a compound of the general formula (II) with a halogen compound of the general formula (III) is conducted ordinarily in a suitable solvent in the presence of a catalyst. As to the solvent used in this reaction is not particularly restricted unless it gives any adverse effects to the reaction, specific examples include ketones such as acetone, methyl ethyl ketone, 3-pentanone and the like; polar solvents such as acetonitrile, dimethylformamide, dimethyl sulfoxide and the like; etc. As to the catalyst used in this reaction, there can be used any of those catalyst which are ordinarily employed in this kind of reaction. Particularly, for example, metal oxides such as silver oxide, barium oxide, mercury oxide and the like are preferably used. It is appropriate that the halogen compound of the general formula (III) be used ordinarily in an amount of 1 to 10 moles, preferably 2 to 5 moles relative to 1 mole of the 3-substituted-2'-deoxy-5-substituted uridine derivative of the general formula (II). The reaction temperature is not particularly restricted, and ordinarily is a room temperature to about 100° C., preferably is about 50° to 80° C. Thus, there is obtained a derivative of the present invention wherein $R_1$ in the general formula (I) is a benzoyl group or a tetrahydrofuranyl group.

Those derivatives of the present invention wherein $R_1$ in the general formula (I) is a hydrogen atom can be prepared by reacting, for example, a compound of the general formula (I) wherein $R_1$ is a benzoyl group, which can be obtained by the above described reaction, with an acid or an alkali to remove the benzoyl group. As to the acid or alkali used in this benzoyl group removing reaction, any acid or alkali compound usually used in an ordinary benzoyl group removing reaction can also be used. Preferably acids include, for example, mineral acids such as hydrochloric acid and the like as well as sulfonic acids such as p-toluenesulfonic acid and the like. Preferable alkalis include, for example, inorganic bases such as sodium hydroxide, ammonia and the like; organic bases such as alkyl amines such as n-butylamine and the like; metal alcoholates such as sodium alcoholate, potassium alcoholate and the like; and metal amides such as sodium amide, potassium amide and the like.

The above-mentioned benzoyl group removing reaction is conducted ordinarily in a suitable solvent such as water, an alcohol or the like. The reaction temperature is about 0° to 60° C., preferably is a room temperature or thereabouts. Thus, there is obtained a derivative of the present invention wherein $R_1$ in the general formula (I) is a hydrogen atom.

Among derivatives of the present invention, wherein $R_1$ in the general formula (I) is a tetrahydrofuranyl group can also be prepared by reacting, for example, a derivative of the present invention wherein $R_1$ in the general formula (I) is a hydrogen atom, which is obtained by the above described process, with 2-chlorotetrahydrofuran in the presence of a basic compound. Examples of the base include inorganic bases such as sodium hydroxide, ammonia and the like as well as organic bases such as pyridine, an alkylamine and the like. The above reaction is conducted ordinarily in a suitable solvent such as dimethylformamide, dimethylacetamide or the like. The reaction temperature usually is about $-50°$ to $100°$ C., preferably is $0°$ to $50°$ C. Thus, there is obtained a derivative of the present invention wherein $R_1$ in the general formula (I) is a tetrahydrofuranyl group.

Among derivatives of the present invention wherein $R_1$ in the general formula (I) is a hydrogen atom, any one of $R_3$ and $R_4$ is a hydrogen atom and the other one is a group represented by the general formula (IV),

(IV)

wherein $R_8$ and $R_9$ each are a hydrogen atom or a methyl group, provided that $R_8$ and $R_9$ are not a hydrogen atom at the same time, can be prepared by reacting $F_3TdR$ or FudR with a compound represented by the general formula (V),

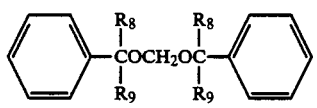
(V)

wherein $R_8$ and $R_9$ each are the same as defined above. This reaction may be conducted in the absence or presence of a solvent, preferably the reaction is conducted in the presence of a solvent. As to the solvent used this reaction is not particularly restricted unless it gives any adverse effect to the reaction. Examples of the solvents include ethers such as ethyl ether, dioxane and the like as well as polar solvents such as chloroform, pyridine, acetonitrile, dimethylformamide and the like. A compound of the general formula (V) is used ordinarily in an amount of 1 to 10 moles, preferably 1 to 4 moles relative to 1 mole of FudR or $F_3TdR$. The above reaction proceeds even in the absence of a catalyst, preferably is conducted in the presence of a catalyst. As to the catalyst used in this reaction include acid catalyst such as hydrochloric acid, p-toluenesulfonic acid, aluminum chloride and the like. The reaction temperature ordinarily is a room temperature to about 100° C., preferably 60° to 80° C.

Derivatives of the present invention prepared according to each of the above-mentioned processes can be isolated and purified by any one of known methods for separation and purification, for example, recrystallization, column chromatography and the like.

2'-Deoxy-5-substituted uridine derivatives of the present invention represented by the general formula (I) are useful as an antitumor agent. In their use as the antitumor agent, they are ordinarily combined with a suitable, pharmaceutically acceptable carrier to be prepared into a pharmaceutical preparation having a form suitable for desired administration purposes. As to the carrier may be, for example, a diluent, a binder, a lubricant, a coloring agent or a disintegrator, which are conventionally used and pharmaceutically acceptable. The pharmaceutical preparation may take a form of tablet, capsule, granule, powder, liquid or the like for oral administration, as well as a form of injection or the like for non-oral administrations such as intravenous injection. The pharmaceutical preparation may also take a form of suppository for intra-rectal administration. The content of the active ingredient (compound of the present invention) per unit form of each pharmaceutical preparation can be appropriately decided so as to be proper for that particular form and is not largely different from those in ordinary pharmaceutical preparations. A preferable content of the active ingredient generally is about 25 to 500 mg per 1 unit. Pharmaceutical preparation of the above forms can be done according to the respective usual methods.

The administration dosage of each pharmaceutical preparations differs naturally from the condition, the weight, the age and the like of a patient to whom the pharmaceutical preparation is to be administered and accordingly can not be restricted.

Hereinunder, there are shown pharmacological tests results, namely, antitumor activity values and toxicity values, of compounds of the present invention. Further, based on therapeutic indexes calculated from these two kinds of values, usefulness of the compounds of the present invention will be explained.

Pharmacological tests (a) Method for determining of antitumor activity value $5 \times 10^6$ Cells of mouse-transplantable tumor Sarcoma 180 were transplanted to each male ICR/JCL-strain mouse (having a weight of 27 to 30 g) subcutaneously at the back. Each test compound dissolved or suspended in 0.1% Tween 80(*)—0.5% CMC solution was orally administered to various test groups each consisting of 7 mice once a day for 7 consecutive days from the next day of tumor transplanting, in an amount of 1.0 ml of solution or suspension per 100 g weight per day. As to a control group, the same Tween 80-CMC solution containing no test compound was orally administered once a day for 7 consecutive days in an amount of 1.0 ml per 100 g weight per day.

(*) (A trademark for a series of surface active agents, which is a polyoxyethylene derivative of fatty acid partial ester of sorbitol anhydride, manufactured by I.C.I. United States, Inc.)

On the tenth day from the tumor transplanting, an average tumor weight for each administration level of each test compound was determined. This weight was compared with an average tumor weight in control group, and the ratio of tumor enhancement inhibition at each administration level of each test compound compared with control group was calculated. From these calculations, the administration level of each test compound at which the ratio of tumor enhancement inhibition become 50% was obtained and the level (amount) was taken as the antitumor activity value of each compound.

(b) Method for determining toxicity value

Hitherto, toxicity values of anti-malignant tumor agents have been calculated on the bases of $LD_{50}$ of test animals, in most cases. However, $LD_{50}$ is measured under serious conditions of test animal far deviating from conditions of patient where drugs are actually used and accordingly $LD_{50}$ does not represent a practical toxicity of drug. Therefore, in the present test, accumulated toxicity, which well represents the toxicity of anti-malignant tumor agents, was focused on and, as an indication for sensitive detection of the accumulated toxicity, inhibition of weight increase of test animal was measured. That is, when antitumor activity value was determined in the above item (a), the weight of each mouse of each test groups for each test compounds was measured daily from the day of tumor transplanting, immediately before administration.

On the day of tumor weight measurement, the average net weight increase of each mouse of each test groups for each test compounds from the day of tumor transplanting was measured. These increases were compared with the average net weight increase of control group and the ratio of net weight increase of each test groups of each test compounds to that of control group was calculated. From these calculations, there was obtained an addition amount of each test compound at which weight increase is inhibited by 50% compared with that of control group, and that amount was taken as a toxicity value of each compound.

(c) Calculation of therapeutic index

By the use of the antitumor activity value (hereinafter referred to as A) and the toxicity value (hereinafter referred to as B) of each compound, which were obtained in the above items (a) and (b), respectively, therapeutic index (hereinafter referred to as C) was calculated in accordance with the following equation.

$$\text{Therapeutic index } (C) = \frac{(B)}{(A)}$$

A larger therapeutic index of a compound means that the compound is better balanced in effect and toxicity and more useful.

In Tables 1-a, 1-b and 1-c are shown the results of the above tests, on compounds of the present invention obtained in each of the Examples which follow (a same numeral was used both in table and example for a same compound) as well as on comparative compounds, namely, $F_3TdR$ and FudR.

TABLE 1

| Compound No. | Antitumor activity value (A) Administraion amount of test compound at which tumor enhancement is inhibited by 50% compared with that of control group (mg/Kg/day) | Toxicity value (B) Administration amount of test compound at which weight increase of test animal is inhibited by 50% compared with that of control group (mg/Kg/day) | Therapeutic index (C) = (B)/(A) |
|---|---|---|---|
| 11 | 18 | 22 | 1.22 |
| 12 | 12 | 17 | 1.42 |
| 13 | 48 | 65 | 1.35 |
| 14 | 40 | 57 | 1.43 |
| 15 | 24 | 41 | 1.71 |
| 16 | 31 | 45 | 1.45 |
| 17 | 45 | 51 | 1.13 |
| 18 | 52 | 60 | 1.15 |
| 21 | 22 | 30 | 1.36 |
| $F_3TdR$ | 68 | 49 | 0.72 |
| 24 | 26 | 36 | 1.38 |
| 25 | 38 | 31 | 0.82 |
| 26 | 50 | 74 | 1.48 |
| 27 | 25 | 35 | 1.40 |
| 28 | 25 | 35 | 1.40 |
| 29 | 48 | 72 | 1.50 |
| 30 | 19 | 32 | 1.68 |
| 31 | 20 | 30 | 1.50 |
| 32 | 19 | 34 | 1.79 |
| 33 | 17 | 32 | 1.88 |
| $F_3TdR$ | 58 | 40 | 0.69 |
| 35 | 51 | 70 | 1.37 |
| 39 | 28 | 67 | 2.39 |
| 40 | 17 | 35 | 2.06 |
| 41 | 13 | 30 | 2.31 |
| FudR | 93 | 71 | 0.76 |

As is obvious from Tables 1-a, 1-b, and 1-c, compounds of the present invention are equal or superior to $F_3TdR$ and FudR in toxicity and far superior to them in antitumor activity. When compared in therapeutic index, compounds of the present invention are very useful.

Next, examples of pharmaceutical preparations of compounds of the present invention will be illustrated.

Example of pharmaceutical preparation-1 (Capsules)

Compound 15, lactose, crystalline cellulose and corn starch are mixed in the following proportion. Further, magnesium stearate is mixed with them in the following proportion. This mixture is filled in capsules by the use of a suitable capsule-filling machine so that one capsule contains about 293 mg of the mixture, whereby an intended capsule product is obtained.

| Capsule formulation | mg/capsule |
| --- | --- |
| Compound 15 | 200.0 |
| Lactose | 30.0 |
| Crystalline cellulose | 50.0 |
| Corn starch | 10.0 |
| Magnesium stearate | 3.0 |
| | 293.0 |

Example of pharmaceutical preparation-2 (Granules)

Compound 40, lactose, crystalline cellulose and corn starch are mixed in the following proportion. Thereto is added a 10%-ethanol solution containing hydroxypropyl cellulose and they are kneaded. Then, by the use of an appropriate granulator, the kneaded mixture is made into granules. After drying, the granules are made uniform so as to have granular size of 12 to 42 meshes. Subsequently, the granules are coated with hydroxypropyl methyl cellulose in the following proportion by the use of a suitable coating machine. The coated granules are again made uniform so as to have granular size of 12 to 42 meshes, whereby a granule product is obtained.

| Granule formulation | mg/granule |
| --- | --- |
| Compound 40 | 200.0 |
| Lactose | 200.0 |
| Crystalline cellulose | 311.0 |
| Corn starch | 200.0 |
| Hydroxypropyl cellulose | 10.0 |
| Hydroxypropyl methyl cellulose | 70.0 |
| Fatty acid monoglyceride | 3.5 |
| Titanium dioxide | 5.5 |
| | 1,000.0 |

Example of pharmaceutical preparation-3 (Tablets)

Compound 33, corn starch and calcium cellulose glycolate are mixed in the following proportion. Thereto is added a 10%-ethanol solution containing hydroxypropyl cellulose, and they are kneaded. The kneaded mixture is made into granules by the use of an appropriate granulator. After drying, the granules are mixed with magnesium stearate and silicic acid anhydride in the following proportion and then the mixture is made into tablets by the use of a suitable tablet machine. The tablets are coated with hydroxypropyl methyl cellulose, whereby an intended tablet product is obtained

| Tablet formulation | mg/tablet |
| --- | --- |
| Compound 33 | 200.0 |
| Corn starch | 5.0 |
| Calcium cellulose glycolate | 20.0 |
| Hydroxypropyl cellulose | 2.0 |
| Magnesium stearate | 2.5 |
| Silicic acid anhydride | 2.5 |
| Hydroxypropyl methyl cellulose | 19.999 |
| Polyethylene glycol 6000 | 0.001 |
| Titanium oxide | 2.0 |
| | 254 |

Example of pharmaceutical preparation-4 (Suppository)

Witepzol W-35 (trademark, for a suppository base material manufactured by Dynamite Nobel Co.) is melted at about 60° C. and then kept at about 45° C. This is mixed with compound 12 in the following proportion. The mixture is molded into suppositories each of 1 g by the use of a suitable suppository-manufacturing machine.

| Suppository formulation | mg/suppository |
| --- | --- |
| Compound 12 | 400.0 |
| Witepzol W-35 | 600.0 |
| | 1,000.0 |

Hereinunder, Reference Examples and Examples are illustrated. Reference Examples are for preparation of raw materials of the present invention compounds, namely, 3-benzoyl-2'-deoxy-5-trifluoromethyluridine, 3-(2-tetrahydrofuranyl)-2'-deoxy-5-trifluoromethyluridine and 3-benzoyl-2'-deoxy-5-fluorouridine. Examples are for preparation of compounds of the present invention. With respect to the present invention compounds produced in each Example, in Table 2 are shown their chemical structures; in Table 3 are shown their yields, appearances or melting points, and elemental analyses [values given in parenthesis are calculated ones and values with no parenthesis are measured ones]; and in Table 4 are shown their physicochemical constants (NMR spectrum analysis results, NMR $\delta$ ppm). In Table 4, NMR measurement was made using TMS as an internal standard in DMSO-$d_6$.

REFERENCE EXAMPLE 1

Preparation of 3-benzoyl-2'-deoxy-5-trifluoromethyluridine 12 grams of 2'-deoxy-5-trifluoromethyluridine was dissolved in 30 ml of dimethylacetamide. Thereto was added 8 ml of triethylamine, and further to the mixture being cooled with ice-water was added 5.6 g of benzoyl chloride. The whole mixture was stirred overnight. The reaction mixture was subjected to filtration, the resulting filtrate was subjected to evaporation and the residue was dissolved in ether. To the ether solution being stirred was slowly added water. The resulting precipitate was collected by filtration. The precipitate collected was recrystallized from ether-petroleum ether. The yield was 8.0 g. M.p. 144.5° to 146° C.

REFERENCE EXAMPLE 2

Preparation of 3-(2-tetrahydrofuranyl)-2'-deoxy-5-trifluoromethyluridine 5.92 Grams of 2'-deoxy-5-trifluoromethyluridine was dissolved in 40 ml of dry dimethylacetamide. Thereto was added 2.23 g of triethylamine and the mixture was ice-cooled. Thereto was added dropwise a dry dimethylacetamide solution containing 2.34 g of 2-chlorotetrahydrofuran prepared just prior to use, and the mixture was stirred overnight. The reaction mixture was subjected to filtration and the resulting filtrate was subjected to evaporation. The residue was extracted with chloroform and the extract was dried with anhydrous sodium sulfate. The solvent in the extract was removed by evaporation to obtain an oily residue. The residue was treated by a silica gel column chromatography (developing solvent: chloroform/ethanol=20/1). The eluate was recrystallized from ethanol-petroleum ether to obtain 2.80 g of the desired product. Melting point: 127°–128° C.

REFERENCE EXAMPLE 3

Preparation of 3-benzoyl-2'-deoxy-5-fluorouridine

15 Grams of 2'-deoxy-5-fluoro uridine (FudR) was dissolved in 45 ml of dimethylacetamide. Thereto was added 9 ml of triethylamine. To the mixture being cooled with ice-water was added 8.6 g of benzoyl chloride and the whole mixture was stirred overnight. The reaction mixture was subjected to filtration. The resulting filtrate was subjected to evaporation to obtain the residue, and water was added to the residue. The aqueous solution was extracted with ethyl acetate, and the organic layer was dried with anhydrous sodium sulfate. The dried ethyl acetate solution was concentrated and the residue was recrystallized from ethanol to obtain the desired compound. The yield was 10.5 g. M.p. 126° to 127° C.

EXAMPLE 1

4.92 Grams of 3-benzoyl-2'-deoxy-5trifluoromethyluridine was dissolved in 40 ml of methyl ethyl ketone. Thereto were added 7.86 g of 4-chlorobenzyl bromide and 7.38 g of silver oxide, and the mixture was refluxed for 1.5 hours. The reaction mixture was filtered and the filtrate was concentrated. The residue was subjected to silica gel column chromatography (developing solvent:benzene-acetone=10:1). The eluate was subjected to recrystallization from ethanol to obtain 1.09 g (yield: 16.2%) of 3-benzoyl-2'-deoxy-5'-O-(4-chlorobenzyl)-5-trifluoromethyluridine (compound 1) having a melting point of 159° to 160.5° C. and further 2.90 g (yield: 43.2%) of amorphous 3-benzoyl-2'-deoxy-3'-O-(4-chlorobenzyl)-5-trifluoromethyluridine (compound 2) having a melting point of 164° to 165° C.

EXAMPLE 2

Compounds 3 and 4 were synthesized respectively in a manner similar to that of Example 1.

EXAMPLE 3

4.00 Grams of 3-benzoyl-2'-deoxy-5-trifluoromethyluridine was dissolved in 40 ml of methyl ethyl ketone. Thereto were added 5.02 g of 4-methoxybenzyl bromide and 5.7 g of silver oxide. The mixture was heated to 60° C. and stirred for 12 hours. The reaction mixture was filtered and the filtrate was concentrated. The residue was subjected to silica gel column chromatography (developing solvent: benzene-acetone=10:1). The eluate was subjected to recrystallization from benzene to obtain 2.07 g (yield: 39.8%) of 3-benzoyl-2'-deoxy-3'-O-(4-methoxybenzyl)-5-trifluoromethyluridine (compound 8) having a melting point of 142° to 143° C. The eluate was further subjected to recrystallization from acetonebenzene to obtain 0.64 g (yield: 12.4%) of 3-benzoyl-2'-deoxy-5'-O-(4-methoxybenzyl)-5-trifluoromethyluridine (compound 7) having a melting point of 152° to 153° C.

EXAMPLE 4

Compounds 5, 6, 9 and 10 were synthesized respectively in a manner similar to that of Example 3.

EXAMPLE 5

3.66 Grams of 3-(2-tetrahydrofuranyl)-2'-deoxy-5-trifluoromethyluridine was dissolved in 40 ml of acetone. Thereto were added 5.13 g of benzyl bromide and 5.79 g of silver oxide. The mixture was stirred for 5 hours with refluxing. The reaction mixture ws filtered and the filtrate was concentrated. The residue was subjected to silica gel column chromatography (developing solvent: chloroform-methanol=40:1). The eluate was recrystallized from dichloromethane-petroleum ether to obtain 0.19 g (yield: 4.1%) of 3-(2-tetrahydrofuranyl)-2'-deoxy-5'-O-benzyl-5-trifluoromethyluridine (compound 21) having the melting point of 145° to 147° C.

EXAMPLE 6

0.40 Gram of 3-benzoyl-2'-deoxy-5'-O-(2-methylbenzyl)-5-trifluoromethyluridine (compound 3) was dissolved in 12 ml of methanol. Thereto was added 1.2 ml of 30% ammonia water, and the mixture was stirred for 30 minutes at a room temperature. The reaction mixture was subjected to evaporation. The residue was subjected to silica gel column chromatography (developing solvent: benzene-acetone=5:1). The eluate was subjected to recrystallization from ethanol-petroleum ether to obtain 0.29 g (yield: 91.7%) of 2'-deoxy-5'-O-(2-methylbenzyl)-5-trifluoromethyluridine (compound 13) having the melting point of 178° to 179° C.

EXAMPLE 7

Compounds 11, 12, 14 and 45 were prepared respectively in a procedure similar to that of Example 6.

EXAMPLE 8

4.00 Grams of 3-benzoyl-2'-deoxy-5-trifluoromethyluridine was dissolved in 40 ml of methyl ethyl ketone. Thereto were added 6.3 g of 3-methylbenzyl bromide and 5.79 g of silver oxide. The mixture was heated to 65° C. and stirred for 2.5 hours. The reaction mixture was filtered and the filtrate was concentrated. The residue was extracted with chloroform and the extract was dried with anhydrous sodium sulfate. The solvent was removed by evaporation to obtain in oily residue.

The residue was admixed with 60 ml of ethanol and dissolved therein. Thereto was added 6 ml of 30% ammonia water, and the mixture was stirred overnight at a room temperature. The reaction solvent was removed by evaporation and the residue was extracted with dichloromethane. The organic layer was dried with anhydrous sodium sulfate. The solvent was removed by evaporation to obtain an oily residue. This residue was subjected to silica gel column chromatography (developing solvent: benzene-acetone—10:1) to first obtain 0.28 g (yield: 7.0%) of amorphous 2'-deoxy-3'-O-(3-methylbenzyl)-5-trifluoromethyluridine (compound 16). By switching the developing solvent to benzene-acetone=5:1 and subjecting the eluate to recrystallization from benzene-petroleum ether, there was obtained 0.085 g (yield: 2.1%) of 2'-deoxy-5'-O-(3-methylbenzyl)-5-trifluoromethyluridine (compound 15) having the melting point of 169° to 171° C.

EXAMPLE 9

To 0.60 g of 3-benzoyl-2'-deoxy-3'-O-(4-methoxybenzyl)-5-trifluoromethyluridine (compound 8) were added 10 ml of ethanol and 1 ml of 30% ammonia water. The mixture was stirred for 1 hour at a room temperature. The reaction mixture was subjected to evaporation and the residue was extracted with dichloromethane. The extract was dried with anhydrous sodium sulfate and the solvent was removed by evaporation. The residue was subjected to silica gel column chromatography (developing solvent: benzene-acetone=10:1) to obtain 0.34 g (yield: 70.4%) of 2'-deoxy-3'-O-(4-methoxybenzyl)-5-trifluoromethyluridine (compound 18) in the form of viscous oily substance.

EXAMPLE 10

Compounds 17, 19 and 20 were obtained respectively in a manner similar to that of Example 9.

EXAMPLE 11

0.87 Gram of 2'-deoxy-5'-O-benzyl-5-trifluoromethyluridine was dissolved in 6 ml of dry dimethylacetamide. Thereto was added 0.25 g of triethylamine, and they were ice-cooled. Thereto was added dropwise a dry dimethylacetamide solution containing 0.264 mg of 2-chlorotetrahydrofuran prepared just prior to use, and the mixture was stirred overnight. The reaction mixture was filtered and the filtrate was subjected to evaporation. The residue was subjected to silica gel column chromatography (developing solvent: chloroform-methanol=20:1). The eluate was recrystallized from dichloromethane-petroleum ether to obtain 0.70 g (yield: 68.2%) of 3-(2-tetrahydrofuranyl)-2'-deoxy-5'-O-benzyl-5-trifluoromethyluridine (compound 21) having the melting point of 145° to 147° C.

EXAMPLE 12

1.00 Gram of 2'-deoxy-5-trifluoromethyluridine was dissolved in 15 ml of 1,4-dioxane. Thereto were added 2.50 g of bis-($\alpha,\alpha$-dimethylbenzyloxy)methane and 38 mg of toluenesulfonic acid anhydride. They were heated to 60° C. and stirred for 3.5 hours. The reaction mixture was subjected to evaporation. The residue was subjected to silica gel column chromatography wherein a developing solvent of chloroform-methanol (20:1) was first used for preliminary separation and then a developing solvent of benzene-acetone (10:1) was used, to obtain 0.40 g (yield: 29.2%) of hygroscopic and amorphous 2'-deoxy-5'-O-($\alpha,\alpha$-dimethylbenzyl)-5-trifluoromethyluridine (compound 22) and 0.28 g (yield: 20.4%) of hygroscopic and amorphous 2'-deoxy-3'-O-($\alpha,\alpha$-dimethylbenzyl)-5-trifluoromethyluridine (compound 23).

EXAMPLE 13

2 Grams of 3-benzoyl-2'-deoxy-5-trifluoromethyluridine was dissolved in 20 ml of acetone. Thereto were added 2.3 g of ethyl iodide and 5.8 g of silver oxide, and the mixture was refluxed for 5 hours. The reaction mixture was filtered and the filtrate was subjected to evaporation. The residue was subjected to silica gel column chromatography (developing solvent: chloroform-ethanol=20:1) to obtain 980 mg (yield: 46%) of 3-benzoyl-2'-deoxy-5'-O-ethyl-5-trifluoromethyluridine (compound 24). Further, by recrystallizing the eluate from ethanol, there was also obtained 340 mg (yield: 16%) of 3-benzoyl-2'-deoxy-3'-O-ethyl-5-trifluoromethyluridine (compound 2) having a melting point of 156° to 157° C.

EXAMPLE 14

Compound 26 was obtained in a manner similar to that of Example 13.

EXAMPLE 15

1 Gram of 3-benzoyl-2'-deoxy-5'-O-ethyl-5-trifluoromethyluridine (compound 24) was dissolved in 20 ml of ethanol. Thereto was added 2 ml of 30% ammonia water, and the mixture was stirred for 1 hour at a room temperature. The reaction mixture was subjected to evaporation and the residue was subjected to silica gel column chromatography (developing solvent: benzene-acetone=5:1). The eluate was recrystallized from ethanol to obtain 320 mg (yield: 43%) of 2'-deoxy-5'-O-ethyl-5-trifluoromethyluridine (compound 30) having a melting point of 188° to 189.5° C.

EXAMPLE 16

Compounds 32 and 42 were obtained respectively in a manner similar to that of Example 15.

EXAMPLE 17

4 Grams of 3-benzoyl-2'-deoxy-5-trifluoromethyluridine was dissolved in 20 ml of acetone. Thereto were added 7.8 g of ethyl iodide and 6.9 g of silver oxide, and the mixture was refluxed for 5 hours. The reaction mixture was filtered and the filtrate was subjected to evaporation. The residue was dissolved in 20 ml of ethanol. To the solution was added 2 ml of 30% ammonia water, and this mixture was stirred for 1 hour at a room temperature. The solvent was removed by evaporation and the residue was subjected to silica gel column chromatography (developing solvent: chloroform-ethanol=25:1). The eluate was recrystallized from ethanol to obtain 290 mg (yield: 9%) of 2'-deoxy-3'-O-ethyl-5-trifluoromethyluridine (compound 31) having a melting point of 183° to 184° C.

EXAMPLE 18

Compound 29 was obtained in a manner similar to that of Example 17.

EXAMPLE 19

6 Grams of 3-benzoyl-2'-deoxy-5-trifluoromethyluridine was dissolved in 60 ml of methyl ethyl ketone. Thereto were added 7.7 g of benzyl bromide and 8.7 g of silver oxide, and they were refluxed for 2 hours. The reaction mixture was filtered and the solvent was removed by evaporation. The residue was subjected to silica gel column chromatography (developing solvent: benzene-acetone=10:1). By recrystallizing each eluate from benzene, there were obtained 3.24 g (yield: 44%) of 3-benzoyl-3'-O-benzyl-2'-deoxy-5-trifluoromethyluridine (compound 28) having the melting point of 160.5° to 162.5° C. and 0.7 g (yield: 9.5%) of 3-benzoyl-5'-O-benzyl-2'-deoxy-5-trifluoromethyluridine (compound 27) having the melting point of 153.5° to 155° C.

EXAMPLE 20

557 Milligrams of 3-benzoyl-3'-O-benzyl-2'-deoxy-5-trifluoromethyluridine was dissolved in 12 ml of ethanol-acetone (5:1). Thereto was added 1.2 ml of 30% ammonia water, and the mixture was stirred for 2.5 hours at a room temperature. The reaction mixture was filtered and the solvent in the filtrate was removed by evaporation. The residue was subjected to silica gel column chromatography (developing solvent: benzene-acetone=10:1). The eluate was recrystallized from benzene to obtain 235 mg (yield: 53.6%) of 3'-O-benzyl-2'-deoxy-5-trifluoromethyluridine (compound 33) having the melting point of 157° to 158.5° C.

EXAMPLE 21

3.5 Grams of 3-benzoyl-2'-deoxy-5-fluorouridine was dissolved in 40 ml of methyl ethyl ketone. Thereto were added 4.7 g of ethyl iodide and 5.8 g of silver oxide, and the mixture was stirred for 9 hours at 65° to 70° C. The reaction mixture was filtered and the solvent in the filtrate was removed by evaporation. The residue was subjected to silica gel column chromatography (developing solvent: benzene-acetone=10:1).

From the earlier eluate there was obtained 0.86 g (yield: 23%) of 3-benzoyl-2'-deoxy-3'-O-ethyl-5-fluorouridine (compound 34) as an oily substance.

The later eluate was subjected to recrystallization from benzene to obtain 1.48 g (yield: 39%) of 3-benzoyl-2'-deoxy-5'-O-ethyl-5-fluorouridine (compound 35) having the melting point of 143° to 144° C.

EXAMPLE 22

Compounds 36, 37, 44 and 46 were synthesized respectively in a manner similar to that of Example 21.

EXAMPLE 23

1.38 Grams of 3-benzoyl-2'-deoxy-3'-O-benzyl-5-fluorouridine (compound 36) was dissolved in a mixed solvent consisting of 30 ml of ethanol and 3 ml of acetone. Thereto was added 3 ml of 30% ammonia water, and the mixture was stirred for 1 hour at a room temperature. The reaction mixture was subjected to evaporation and the residue thus obtained was subjected to silica gel column chromatography (developing solvent: chloroform-ethanol=25:1) to obtain 0.68 g (yield: 65%) of oily 2'-deoxy-3'-O-benzyl-5-fluorouridine (compound 40).

EXAMPLE 24

Compounds 38, 39, 41, 43, 47 and 48 were synthesized respectively in a manner similar to that of Example 23.

Chemical structures of $R_1$, $R_2$, $R_3$ and $R_4$ in the general formula (I) are shown with respect to compounds are shown in Table 2.

Yield (%), appearance, melting point (°C.), and elementary analysis data of compounds are shown in Table 3.

NMR spectrum data of compounds are shown in Table 4 as follows.

TABLE 2

| Compound No. | Chemical structure of $R_1$, $R_2$, $R_3$ and $R_4$ in the general formula (I) | | | |
|---|---|---|---|---|
| | $R_1$ | $R_2$ | $R_3$ | $R_4$ |
| 1 | phenyl-C(=O)- | $-CF_3$ | Cl-C6H4-CH2- (para) | H |
| 2 | " | $-CF_3$ | H | Cl-C6H4-CH2 (para) |
| 3 | " | $-CF_3$ | o-CH3-C6H4-CH2- | H |
| 4 | " | $-CF_3$ | H | o-CH3-C6H4-CH2- |
| 5 | phenyl-C(=O)- | $-CF_3$ | m-CH3-C6H4-CH2- | H |
| 6 | " | $-CF_3$ | H | m-CH3-C6H4-CH2- |
| 7 | " | $-CF_3$ | CH3O-C6H4-CH2- (para) | H |

TABLE 2-continued

| Compound No. | Chemical structure of $R_1$, $R_2$, $R_3$ and $R_4$ in the general formula (I) | | | |
|---|---|---|---|---|
| | $R_1$ | $R_2$ | $R_3$ | $R_4$ |
| 8 | " | —$CF_3$ | H | 4-$CH_3O$-$C_6H_4$-$CH_2$— |
| 9 | " | —$CF_3$ | 2-$NO_2$-$C_6H_4$-$CH_2$— | H |
| 10 | $C_6H_5$-CO— | —$CF_3$ | H | 2-$NO_2$-$C_6H_4$-$CH_2$— |
| 11 | H | —$CF_3$ | 4-Cl-$C_6H_4$-$CH_2$— | H |
| 12 | " | —$CF_3$ | H | 4-Cl-$C_6H_4$-$CH_2$— |
| 13 | " | —$CF_3$ | 2-$CH_3$-$C_6H_4$-$CH_2$— | H |
| 14 | " | —$CF_3$ | H | 2-$CH_3$-$C_6H_4$-$CH_2$— |
| 15 | " | —$CF_3$ | 3-$CH_3$-$C_6H_4$-$CH_2$— | H |
| 16 | H | —$CF_3$ | H | 3-$CH_3$-$C_6H_4$-$CH_2$— |
| 17 | " | —$CF_3$ | 4-$CH_3O$-$C_6H_4$-$CH_2$— | H |
| 18 | " | —$CF_3$ | H | 4-$CH_3O$-$C_6H_4$-$CH_2$— |

TABLE 2-continued

| Compound No. | R₁ | R₂ | R₃ | R₄ |
|---|---|---|---|---|
| 19 | " | —CF₃ | 2-NO₂-C₆H₄—CH₂— | H |
| 20 | " | —CF₃ | H | 2-NO₂-C₆H₄—CH₂— |
| 21 | 2-tetrahydrofuryl | —CF₃ | C₆H₅—CH₂— | H |
| 22 | H | —CF₃ | C₆H₅—C(CH₃)₂— | H |
| 23 | " | —CF₃ | H | C₆H₅—C(CH₃)₂— |
| 24 | C₆H₅—C(=O)— | —CF₃ | —CH₂CH₃ | H |
| 25 | " | —CF₃ | H | —CH₂CH₃ |
| 26 | " | —CF₃ | —CH₂CH₂CH₂CH₃ | H |
| 27 | " | —CF₃ | —CH₂—C₆H₅ | H |
| 28 | C₆H₅—C(=O)— | —CF₃ | H | —CH₂—C₆H₅ |
| 29 | H | —CF₃ | —CH₃ | H |
| 30 | " | —CF₃ | —CH₂CH₃ | H |
| 31 | " | —CF₃ | H | —CH₂CH₃ |
| 32 | " | —CF₃ | —CH₂—C₆H₅ | H |
| 33 | " | —CF₃ | H | —CH₂—C₆H₅ |
| 34 | C₆H₅—C(=O)— | —CF₃ | H | —CH₂CH₃ |
| 35 | " | F | —CH₂CH₃ | H |

TABLE 2-continued

| Compound No. | R₁ | R₂ | R₃ | R₄ |
|---|---|---|---|---|
| 36 | " | F | H | —CH₂—C₆H₅ |
| 37 | " | F | —CH₂—C₆H₅ | H |
| 38 | H | F | H | —CH₂CH₃ |
| 39 | " | F | —CH₂CH₃ | H |
| 40 | H | F | H | —CH₂—C₆H₅ |
| 41 | " | F | —CH₂—C₆H₅ | H |
| 42 | " | —CF₃ | —(CH₂)₃CH₃ | H |
| 43 | " | F | H | —CH₂CH₂—C₆H₅ |
| 44 | C₆H₅—CO— | F | —CH₂CH=CH₂ | H |
| 45 | H | —CF₃ | H | —CH₂CH=CH₂ |
| 46 | C₆H₅—CO— | F | H | —CH(C₆H₅)₂ |
| 47 | H | F | H | —(CH₂)₉CH₃ |
| 48 | H | F | H | —CH₂CH(CH₃)₂ |

TABLE 3

| Compound No. | Yield (%) | Appearance or M.P. (°C.) | Elementary analysis H % | C % | N % |
|---|---|---|---|---|---|
| 1 | 16.2 | 159–160.5 | 3.96 (3.79) | 54.36 (54.19) | 5.04 (5.26) |
| 2 | 43.2 | 164–165 | | | |
| 3 | 15.0 | 146–147 | | | |
| 4 | 49.3 | 173.5–174.5 | 4.83 (4.59) | 59.49 (59.52) | 5.38 (5.55) |
| 5 | 8.8 | Oily substance | | | |
| 6 | 33.1 | 123–125 | 4.87 (4.59) | 59.77 (59.52) | 5.38 (5.55) |
| 7 | 12.4 | 152–153 | 4.44 (4.45) | 57.96 (57.69) | 5.41 (5.38) |
| 8 | 39.8 | 142–143 | 4.63 (4.45) | 57.79 (57.69) | 5.42 (5.38) |
| 9 | 10.2 | 60 | | | |
| 10 | 32.4 | 160.5–164.5 | | | |

TABLE 3-continued

| Compound No. | Yield (%) | Appearance or M.P. (°C.) | Elementary analysis | | |
|---|---|---|---|---|---|
| | | | H % | C % | N % |
| 11 | 67.5 | 186–187.5 | 3.64 (3.83) | 48.60 (48.52) | 6.77 (6.65) |
| 12 | 72.8 | 160–161 | | | |
| 13 | 91.7 | 178–179 | 4.86 (4.78) | 53.74 (54.00) | 6.78 (6.99) |
| 14 | 78.8 | Amorphous powder | | | |
| 15 | 52.0 | 169–171 | 4.91 (4.79) | 53.90 (54.00) | 7.08 (6.99) |
| 16 | 81.6 | Amorphous powder | | | |
| 17 | 70.1 | 174.5–176 | 4.83 (4.60) | 51.74 (51.93) | 6.78 (6.73) |
| 18 | 70.4 | Oily substance | | | |
| 19 | 16.4 | Oily substance | | | |
| 20 | 21.6 | Oily substance | | | |
| 21 | 68.2 | 145–147 | 5.07 (5.08) | 55.12 (55.26) | 6.22 (6.14) |
| 22 | 29.2 | Amorphous powder | | | |
| 23 | 20.4 | Amorphous powder | | | |
| 24 | 46 | Amorphous powder | 4.76 (4.47) | 53.00 (53.27) | 6.42 (6.54) |
| 25 | 16 | 156–157 | 4.82 | 53.12 | 6.33 |
| | | | (4.47) | (53.27) | (6.54) |
| 26 | 38 | Oily substance | | | |
| 27 | 9.5 | 153.5–155 | 4.34 (4.32) | 58.90 (58.78) | 5.78 (5.71) |
| 28 | 44 | 160.5–162..5 | 4.39 (4.32) | 58.63 (58.78) | 5.73 (5.71) |
| 29 | 47 | 205–206 | | | |
| 30 | 43 | 188–189.5 | 4.60 (4.66) | 44.20 (44.45) | 8.52 (8.64) |
| 31 | 9 | 183–184 | 4.74 (4.66) | 44.67 (44.45) | 8.70 (8.64) |
| 32 | 57 | 175.5–176.5 | 4.54 (4.44) | 52.82 (52.85) | 7.28 (7.25) |
| 33 | 53.6 | 157–158.5 | 4.65 (4.44) | 52.99 (52.85) | 7.25 (7.25) |
| 34 | 23 | Oily substance | | | |
| 35 | 39 | 143–144 | | | |
| 36 | 25 | Oily substance | | | |
| 37 | 28 | Oily substance | | | |
| 38 | 42 | Oily substance | | | |
| 39 | 53 | Oily substance | | | |
| 40 | 65 | Oily substance | | | |
| 41 | 49 | Oily substance | | | |
| 42 | 46 | Oily substance | | | |

TABLE 4

| Compound No. | N³—H | H⁶ | H¹' | H³' H⁴' | H⁵' | H²' | —OCH₂— | 3'-OH | 5'-OH | Others |
|---|---|---|---|---|---|---|---|---|---|---|
| 1 | | 8.56 d | 6.06 t | 4.12-4.44 m, 3.88-4.18 m | 3.44-3.88 m | 2.08-2.4 m | 4.57 m | 5.40 d | | benzoyl-CO 7.4-8.2, m; ClC₆H₄CH₂— 7.36-7.40 4H, m |
| 2 | | 8.95 s | 6.09 t | 4.04-4.40 m | 3.60-3.88 m | 2.32-2.60 m | 4.54 s | | 5.32 broad | benzoyl-CO 7.4-8.2, m; ClC₆H₄CH₂— 7.36-7.46 |
| 3 | | 8.54 d | 6.05 t | 4.12-4.36 m, 3.92-4.12 m | 3.44-3.88 m | 2.08-2.40 m | 4.58 d | 5.39 d | | benzoyl-CO 7.4-8.2, m; (CH₃)C₆H₃CH₂— 7.0-7.4 m; 2.28, s |
| 4 | | 8.97 s | 6.08 t | 4.04-4.20 m | 3.52-3.88 m | 2.36-2.06 m | 4.53 s | | 5.28-5.60 broad | benzoyl-CO 7.4-8.2, m; (CH₃)C₆H₃CH₂— 7.0-7.4 m; 2.28, s |
| 5 | | 8.60 d | 6.05 t | 4.29 m | 9.4-3.9 m | 2.1-2.5 m | 4.54 s | 5.39 d | | benzoyl-CO 7.4-8.2, m; (CH₃)C₆H₃CH₂— 6.9-7.4 m; 2.29, s |
| 6 | | 8.97 d | 6.09 t | 4.04-4.4 m | 3.5-3.9 m | 2.1-2.5 m | 4.51 s | | 5.41 t | benzoyl-CO 7.4-8.2, m; (CH₃)C₆H₃CH₂— 6.9-7.4 m; 2.29, s |

TABLE 4-continued

| Compound No. | N³—H | H⁶ | H¹' | H³' | H⁴' | H⁵' | H²' | —OCH₂— | 3'-OH | 5'-OH | Others |
|---|---|---|---|---|---|---|---|---|---|---|---|
| 7 | | 8.62 d | 6.05 t | 4.28 m | 4.01 q | 3.4–3.8 m | 2.1–2.5 m | 4.50 s | 5.39 d | | benzoyl—CO—C₆H₅ 7.4-8.2, m; methoxybenzyl ring with CH₃O 6.90, d and CH₂— 7.23, d; CH₃O 3.74, s |
| 8 | | 8.95 d | 6.07 t | 4.04–4.3 m | | 3.4–3.8 m | 2.43 t | 4.46 s | | 5.41 t | benzoyl—CO—C₆H₅ 7.4-8.2, m; methoxybenzyl ring with CH₃O 6.90, d and CH₂— 7.27, d; CH₃O 3.74, s |
| 9 | | 8.47 d | 6.09 t | 4.2–4.4 m | 4.09 q | 3.5–4.0 m | 2.35 t | 4.92 s | 5.45 d | | aromatic H, 7.4-8.3, m |
| 10 | | 8.97 s | 6.09 t | 4.0–4.4 m | | 3.5–3.9 m | 2.3–2.7 m | 4.89 s | | 5.43 t | aromatic H, 7.4-8.2, m |
| 11 | 11.87 broad | 8.34 d | 6.08 t | 4.12–4.40 m | 3.88–4.08 m | 3.44–3.80 m | 2.08–2.40 t | 4.54 s | 5.37 d | | chlorobenzyl CH₂— 7.26–7.47, m |
| 12 | 11.88 broad | 8.69 s | 6.09 t | 4.04–4.28 m | | 3.52–3.80 m | 2.20–2.40 m | 4.53 s | | 5.20–5.38 broad | chlorobenzyl CH₂— 7.36–7.54, m |

TABLE 4-continued

| Compound No. | N³—H | H⁶ | H¹' | H³' | H⁴' | H⁵' | H²' | —OCH₂— | 3'-OH | 5'-OH | Others |
|---|---|---|---|---|---|---|---|---|---|---|---|
| 13 | 11.96 broad | 8.32 d | 6.08 t | 4.08–4.32 broad | 3.88–4.04 m | 3.40–3.80 m | 2.08–2.40 m | 4.54 d | 5.20–5.48 broad | | 2-methylbenzyl group; CH₂ 7.00–7.36 m; CH₃ 2.26 s |
| 14 | 11.88 broad | 8.71 d | 6.09 t | 4.00–4.32 m | | 3.52–3.84 m | 2.20–2.40 m | 4.52 s | | 5.20–5.40 broad | 2-methylbenzyl group; CH₂ 7.00–7.40 m; CH₃ 2.28 s |
| 15 | 11.89 s | 8.38 d | 6.09 t | 4.26 m | 3.98 m | 3.4–3.8 m | 2.1–2.4 m | 4.50 s | 5.36 d | | 3-methylbenzyl group; CH₂ 7.0–7.4 m; CH₃ 2.29 s |
| 16 | 11.86 s | 8.69 d | 6.10 t | 4.0–4.3 m | | 3.5–3.8 m | 2.2–2.5 m | 4.49 s | | 5.30 t | 3-methylbenzyl group; CH₂ 2.2–2.5 m; CH₃ 2.31 s |
| 17 | 11.66 broad | 8.39 d | 6.07 t | 4.2 m | 3.94 m | 3.4–3.7 m | 2.21 t | 4.46 s | 5.35 d | | 3,5-dimethoxybenzyl group; CH₂ 6.90 d; CH₃O 3.74, s; H 7.23, d |
| 18 | 11.88 s | 8.69 d | 6.08 t | 4.0–4.3 m | | 3.5–3.7 m | 2.2–2.5 m | 4.45 s | | 5.29 t | 3,5-dimethoxybenzyl group; CH₂ 6.91 d; CH₃O 3.75, s; H 7.27, d |

TABLE 4-continued

| Compound No. | N³—H | H⁶ | H¹' | H³' | H⁴' | H⁵' | H²' | —OCH₂— | 3'-OH | 5'-OH | Others |
|---|---|---|---|---|---|---|---|---|---|---|---|
| 19 | 11.87 s | 8.24 d | 6.09 t | 4.27 m | 4.02 m | 3.5–3.9 m | 2.1–2.4 m | 4.88 s | 5.40 d | | NO₂–C₆H₃(H)(H)–CH₂— 7.4–8.1, m |
| 20 | 11.8 broad | 8.70 s | 6.09 t | 4.04–4.3 m | | 3.4–3.9 m | 2.1–2.5 m | 4.88 s | | 5.33 t | NO₂–C₆H₃(H)(H)–CH₂— 7.4–7.8, m |
| 21 | | 8.42 d | 6.07 t | 4.27 m | 4.00 m | +H⁴'' 3.4–3.9 m | +H²'' +H³'' 1.7–2.4 m | 4.55 s | 5.39 d | | tetrahydrofuranyl (O, 1'', 2'', 3'', 4''); aromatic H 7.31, s |
| 22 | 11.93 broad | 8.27 d | 6.08 t | 4.04–4.28 broad | 3.80–4.00 broad | 3.00–3.20 m | 2.12–2.36 m | | 5.00–5.60 broad | | Ph–C(CH₃)₂– 1.49, s; 1.46, s; aromatic H 7.20–7.48, m |
| 23 | 11.84 broad | 8.55 d | 6.07 t | | 3.84–4.08 m | 3.56–3.80 m | 2.00–2.40 m | | | 5.20–5.40 broad | Ph–C(CH₃)₂– 1.52, s; 1.50, s; aromatic H 7.04–7.60, m |
| 24 | — | 8.56 d | 6.05 t | 4.26 m | 4.00 m | 3.68 m | 2.30 m | 3.53 q | 5.39 d | — | C₆H₅–C(=O)– H, 1.15, t, —CH₂CH₃; 7.5–8.3, m |
| 25 | — | 8.99 d | 6.05 t | 3.9–4.2 m | 3.9–4.2 m | 3.68 m | 2.38 m | 3.56 q | — | 5.41 t | C₆H₅–C(=O)– H, 1.12, t, —CH₂CH₃; 7.4–8.2, m |

TABLE 4-continued

| Compound No. | N³—H | H⁶ | H¹' | H³' | H⁴' | H⁵' | H²' | —OCH₂— | NMR 3'-OH | 5'-OH | Others |
|---|---|---|---|---|---|---|---|---|---|---|---|
| 26 | — | 8.51 d | 6.05 t | 4.27 m | 4.03 q | 3.67 m | 2.31 t | 3.48 m | 5.38 | — | 7.5–8.2, m, $-\overset{O}{\underset{\|}{C}}-$ phenyl-H; 1.12–1.7, 0.89 t, —CH₂CH₂CH₂CH₃, —CH₂CH₂CH₂CH₃ |
| 27 | — | 8.61 d | 6.07 t | 4.30 m | 4.0 q | 3.4–3.9 m | 2.2–2.5 m | 4.59 s | 5.40 d | — | 7.4–8.2, m, $-\overset{O}{\underset{\|}{C}}-$ phenyl-H; 7.36, d, —CH₂-phenyl |
| 28 | — | 8.96 d | 6.09 t | 4.4–4.4 m | 4.17 t | 3.5–3.9 m | 2.4–2.6 m | 4.55 s | — | 5.41 t | 7.4–8.2, m, $-\overset{O}{\underset{\|}{C}}-$ phenyl-H; 7.34, s, —CH₂-phenyl |
| 29 | 11.86 b | 8.47 d | 6.07 t | 4.19–4.27 m | 3.90–3.97 m | 3.52–3.59 m | 2.20 t | | 5.35 d | — | —OCH₃ 3.30 s |
| 30 | 11.96 s | 8.34 d | 6.08 t | 4.24 m | 3.97 q | 3.60 m | 2.21 t | 3.49 q | 5.35 d | — | 1.11, t, —CH₂CH₃ |
| 31 | 11.86 s | 8.69 d | 6.04 t | 3.90–4.16 m | 3.90–4.16 m | 3.63 q | 2.27 t | 3.47 q | — | 5.28 t | 1.12, t, —CH₂CH₃ |
| 32 | 11.86 s | 8.38 d | 6.08 t | 4.27 m | 3.97 q | 3.62 m | 2.24 t | 4.55 s | 5.36 d | — | 7.32, s, —CH₂-phenyl |
| 33 | 11.88 s | 8.69 d | 6.10 t | 4.0–4.3 m | 4.0–4.3 m | 3.60 bs | 2.32 t | 4.54 s | — | 5.30 t | 7.34, s, —CH₂-phenyl |

TABLE 4-continued

| Compound No. | N³—H | H⁶ | H¹' | H³' | H⁴' | H⁵' | H²' | —OCH₂— | 3'-OH | 5'-OH | Others |
|---|---|---|---|---|---|---|---|---|---|---|---|
| 34 | — | 8.50 d | 6.06 m | 4.10 m | 3.97 m | 3.5–3.7 m | 2.31 m | 3.48 q | — | 5.33 t | 7.4–8.2, m; (benzoyl group with H's labeled); 1.19, t, —CH₂CH₃ |
| 35 | — | 8.40 d | 6.10 t | 4.1–4.4 m | 3.8–4.0 m | 3.5–3.7 m | 2.1–2.4 m | 3.54 q | 5.39 d | — | 7.4–8.2, m; (benzoyl group); 1.19, t, —CH₂CH₃ |
| 36 | — | 8.52 d | 6.13 m | 4.23 m | 4.11 m | 3.68 m | 2.2–2.5 m | 4.55 s | — | 5.36 t | 7.4–8.2, m; (benzoyl group); 7.34, s, —CH₂— (benzyl) |
| 37 | — | 8.23 d | 6.12 m | 4.31 m | 3.98 m | 3.71 m | 2.1–2.4 m | 4.58 s | 5.40 d | — | 7.4–8.2, m; (benzoyl group); 7.37, s, —CH₂— (benzyl) |
| 38 | 11.85 s | 8.21 d | 6.08 m | 3.9–4.2 m | | 3.5–3.8 m | 2.1–2.4 m | 3.47 q | — | 5.32 t | 1.15, t, —CH₂CH₃ |
| 39 | 11.84 broad | 8.12 d | 6.12 m | 4.23 m | 3.87 q | Around 3.58 | 2.1–2.3 m | 3.50 q | 5.25 broad | — | 1.15, t, —CH₂CH₃ |
| 40 | 11.88 s | 8.69 d | 6.10 m | 4.0–4.3 m | | 3.5–3.7 m | 2.1–2.5 m | 4.54 s | — | 5.30 t | 7.34, s, —CH₂— (benzyl) |

TABLE 4-continued

| Compound No. | NMR | | | | | | | | | |
|---|---|---|---|---|---|---|---|---|---|---|
| | $N^3$—H | $H^6$ | $H^{1'}$ | $H^{3'}$ | $H^{4'}$ | $H^{5'}$ | $H^{2'}$ | —OCH$_2$— | 3'-OH | 5'-OH | Others |
| 41 | 11.88 s | 8.38 d | 6.09 m | 4.27 m | 3.98 m | 3.4–3.8 m | 2.24 t | 4.55 s | 5.40 d | — | 7.32, s —CH$_2$— [phenyl ring with H labels] |
| 42 | 11.89 s | 8.30 d | 6.06 t | 4.22 m | 3.98 m | 3.59 m | 2.20 t | Around 3.4 | 5.35 d | | 1.1–1.8 m —OCH$_2$CH$_2$CH$_2$CH$_3$ 0.86 t —OCH$_2$CH$_2$CH$_2$CH$_3$ |

What is claimed is:

1. A 2'-deoxy-5-substituted uridine derivative represented by the formula (I),

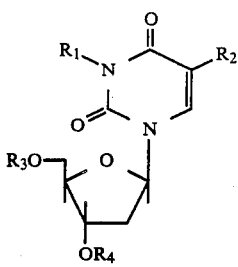

wherein $R_1$ is a hydrogen atom, a benzoyl group or a tetrahydrofuranyl group; $R_2$ is a trifluoromethyl group; and one of $R_3$ and $R_4$ is a hydrogen atom and the other one is a lower alkyl group having 1 to 6 carbon atoms, an alkenyl group having 2 to 6 carbon atoms, a benzyl group or a benzyl group having substituents selected from the group consisting of a halogen atom, an alkyl group having 1 to 4 carbon atoms, an alkoxy group having 1 to 4 carbon atoms and a nitro group.

2. The compound according to claim 1, wherein one of $R_3$ and $R_4$ is a hydrogen atom and the other one is a benzyl group or a benzyl group having substituents selected from the group consisting of a halogen atom, an alkyl group having 1 to 4 carbon atoms, an alkoxy group having 1 to 4 carbon atoms and a nitro group.

3. The compound according to claim 1, wherein $R_1$ is a hydrogen atom or a benzoyl gorup; and one of $R_3$ and $R_4$ is a hydrogen atom and the other one is an alkyl group having 1 to 6 carbon atoms, a benzyl group or a benzyl group substituted by a halogen atom.

4. 2'-Deoxy-5'-O-(4-chlorobenzyl)-5-trifluoromethyluridine, a compound of claim 1.

5. 2'-Deoxy-3'-O-(4-chlorobenzyl)-5-trifluoromethyluridine, a compound of claim 1.

6. 2'-Deoxy-5'-O-(2-methylbenzyl)-5-trifluoromethyluridine, a compound of claim 1.

7. 2'-Deoxy-3'-O-(2-methylbenzyl)-5-trifluoromethyluridine, a compound of claim 1.

8. 2'-Deoxy-5'-O-(3-methylbenzyl)-5-trifluoromethyluridine, a compound of claim 1.

9. 2'-Deoxy-3'-O-(3-methylbenzyl)-5-trifluoromethyluridine, a compound of claim 1.

10. 2'-Deoxy-5'O-(4-methoxybenzyl)-5-trifluoromethyluridine, a compound of claim 1.

11. 2'-Deoxy-3'-O-(4-methoxybenzyl)-5-trifluoromethyluridine, a compound of claim 1.

12. 2'-Deoxy-5'-O-(2-nitrobenzyl)-5-trifluoromethyluridine, a compound of claim 1.

13. 2'-Deoxy-3'-O-(2-nitrobenzyl)-5-trifluoromethyluridine, a compound of claim 1.

14. 2'-Deoxy-5'O-ethyl-5-trifluoromethyluridine, a compound of claim 1.

15. 2'-Deoxy-3'-O-ethyl-5-trifluoromethyluridine, a compound of claim 1.

16. 2'-Deoxy-5'-O-benzyl-5-trifluoromethyluridine, a compound of claim 1.

17. 2'-Deoxy-3'-O-benzyl-5-trifluoromethyluridine, a compound of claim 1.

18. The compound according to claim 1, wherein $R_1$ is a hydrogen atom or a benzoyl group.

* * * * *